United States Patent [19]
Prescott et al.

[11] 3,957,439
[45] May 18, 1976

[54] SURVEYING CONSTANT VALUE CONCENTRATIONS OF HYDROCARBONS IN GROUND WATERS

[75] Inventors: B. Osborn Prescott, Houston, Tex.; Gordon Rittenhouse, deceased, late of Houston, Tex., by Myrtle L. Rittenhouse, executrix; Arley Walters; Harold L. Wise, both of Houston, Tex.

[73] Assignee: Shell Oil Company, Houston, Tex.

[22] Filed: Sept. 22, 1975

[21] Appl. No.: 615,869

[52] U.S. Cl................................. 23/230 EP; 55/55
[51] Int. Cl.².................. B01D 19/00; G01N 33/24
[58] Field of Search................ 23/230 EP; 55/52, 55

[56] References Cited
UNITED STATES PATENTS

| | | | |
|---|---|---|---|
| 2,406,611 | 8/1946 | Kennedy | 23/230 EP |
| 3,345,137 | 10/1967 | McAuliffe | 23/230 EP |
| 3,681,028 | 8/1972 | Mason | 23/230 EP X |

*Primary Examiner*—Robert M. Reese

[57] ABSTRACT

The hydrocarbon content of a ground water in a selected location is measured by flash-distilling a stream of gas from a freshly pumped stream of the water and measuring hydrocarbon concentrations of successive slugs of the gas until the measured values become substantially constant.

10 Claims, 2 Drawing Figures

SURVEYING CONSTANT VALUE CONCENTRATIONS OF HYDROCARBONS IN GROUND WATERS

BACKGROUND OF THE INVENTION

This invention relates to a geochemical exploration process. It is particularly useful in locating subterranean deposits of petroleum materials.

Numerous geochemical exploration processes have been previously proposed. U.S. Pat. No. 2,406,611 (filed over 35 years ago) describes advantages of sampling ground waters rather than soil samples, rock samples, open-water samples, or connate water samples. The use of the ground waters avoids variations in the adsorption of hydrocarbons on solids, contaminations or interactions of hydrocarbons with atmospheric gases, etc. The patented process used ground water samples that were stored in containers for later analysis in a laboratory. U.S. Pat. No. 3,345,137 (filed about 25 years later than the above patent) indicates that bacterially induced chemical changes often significantly alter the hydrocarbon concentrations of ground water samples that are stored for even a few days. It describes an improved process in which a bactericide is added to the samples and concentrations of $C_{2-5}$ and $C_{6-7}$ hydrocarbons are plotted separately.

SUMMARY OF THE INVENTION

The present invention is an improved process for surveying the hydrocarbon content of a ground water. Successive portions of the water are flowed from a selected subsurface location within the ground water habitat to a nearby surface location, at rates such that each portion arrives without significant chemical change. The arriving portions are flash-distilled so that gas inclusive of substantially all materials more volatile than water are separated substantially as soon as the water reaches the surface location. Measurements are made of the concentration of at least one hydrocarbon in successively accumulated slugs of the so-separated gas, substantially as soon as the slugs accumulate. In indicating a hydrocarbon concentration in the ground water in the selected subsurface location, the measurement value used is one that remained substantially constant throughout a plurality of such measurements.

DESCRIPTION OF THE INVENTION

The present invention is, at least in part, premised on the following discovery. In a flowing ground water, measurements can be made of a hydrocarbon concentration which is substantially constant in the water that flows into a selected subsurface location. Several requirements must be met. The ground water must be flowed from the subsurface location to a measuring location fast enough to avoid any significant chemical change. The volatile components of each of a succession of so-arriving portions of the ground water must be flash-distilled and subjected to hydrocarbon concentration measurements under conditions that are substantially the same for each portion that is treated. And, such flash-distillations and concentration-measurements must be continued until the measured values become substantially constant.

The subsurface locations from which the ground water samples are collected can be substantially any within the normal habitat of the ground water. They are preferably locations within wells that encounter ground waters flowing at rates of from about 0.1 to 23 feet per year.

Substantially any flow-inducing means capable of providing water flows in the order of about 2–20 gallons per minute (preferably about 6–10 gpm) can be used to flow the ground water from the sampling location to the measuring location. In general, the rate of flow should be at least fast enough to avoid any significant chemical change in the samples.

The flash-distilling of the ground water to separate a gas to be analyzed is preferably accomplished by flowing a succession of newly-arriving portions of the ground water through an evacuated chamber in which at least some flash-distillation occurs in each portion. The pressure in the chamber and the residence time of each portion of ground water within the chamber are preferably kept substantially constant. Also, the temperature of the chamber is preferably kept substantially constant. It is particularly preferred that the chamber be kept at about the temperature of the subsurface location from which the ground water is being flowed.

Figure 1:
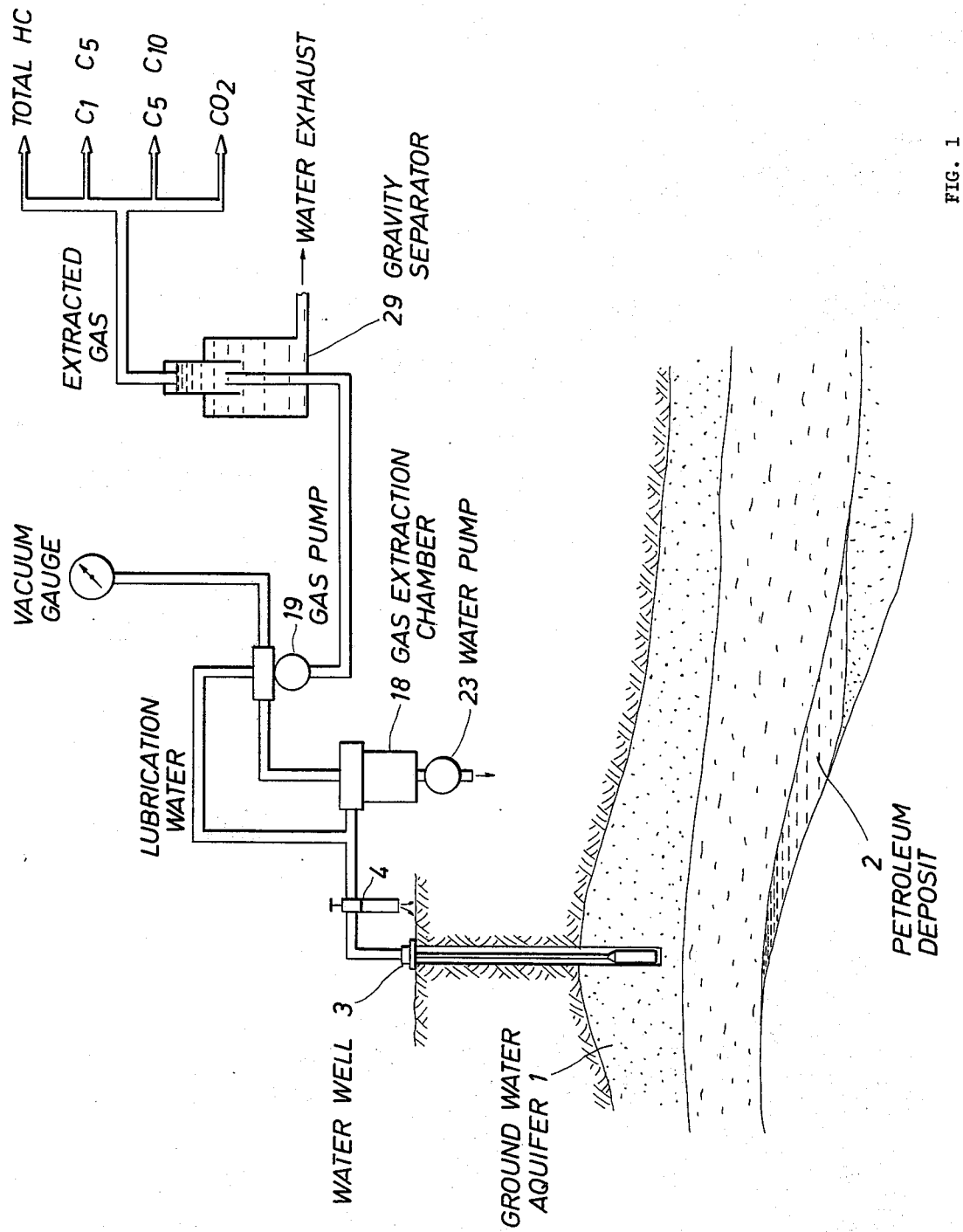
FIG. 1 is a schematic illustration of surveying a ground water aquifer being in accordance with this invention.

FIG. 1 illustrates a particularly suitable arrangement for using the present invention. It shows a ground water aquifer 1 overlying a petroleum deposit 2. Water from the aquifer is produced, by a conventional pumping arrangement, from a water well 3. The water is preferably produced at a rate exceeding that needed for analysis and the excess is metered off with a conventional metering valve 4. In the gas extracting and analyzing system a gas pump 19 draws the water into a gas extraction chamber 18 from which the excess water is removed by a water pump 23. The extracted gas is freed of water in a gravity separator 29 and subjected to hydrocarbon analysis. In a preferred embodiment hydrogen flame chromatographs are employed for determinations of respectively total hydrocarbons, hydrocarbons of from 1–5 carbon atoms, and hydrocarbons of from 5–10 carbon atoms. And, a separate on-site analysis is also made of carbon dioxide.

Figure 2:
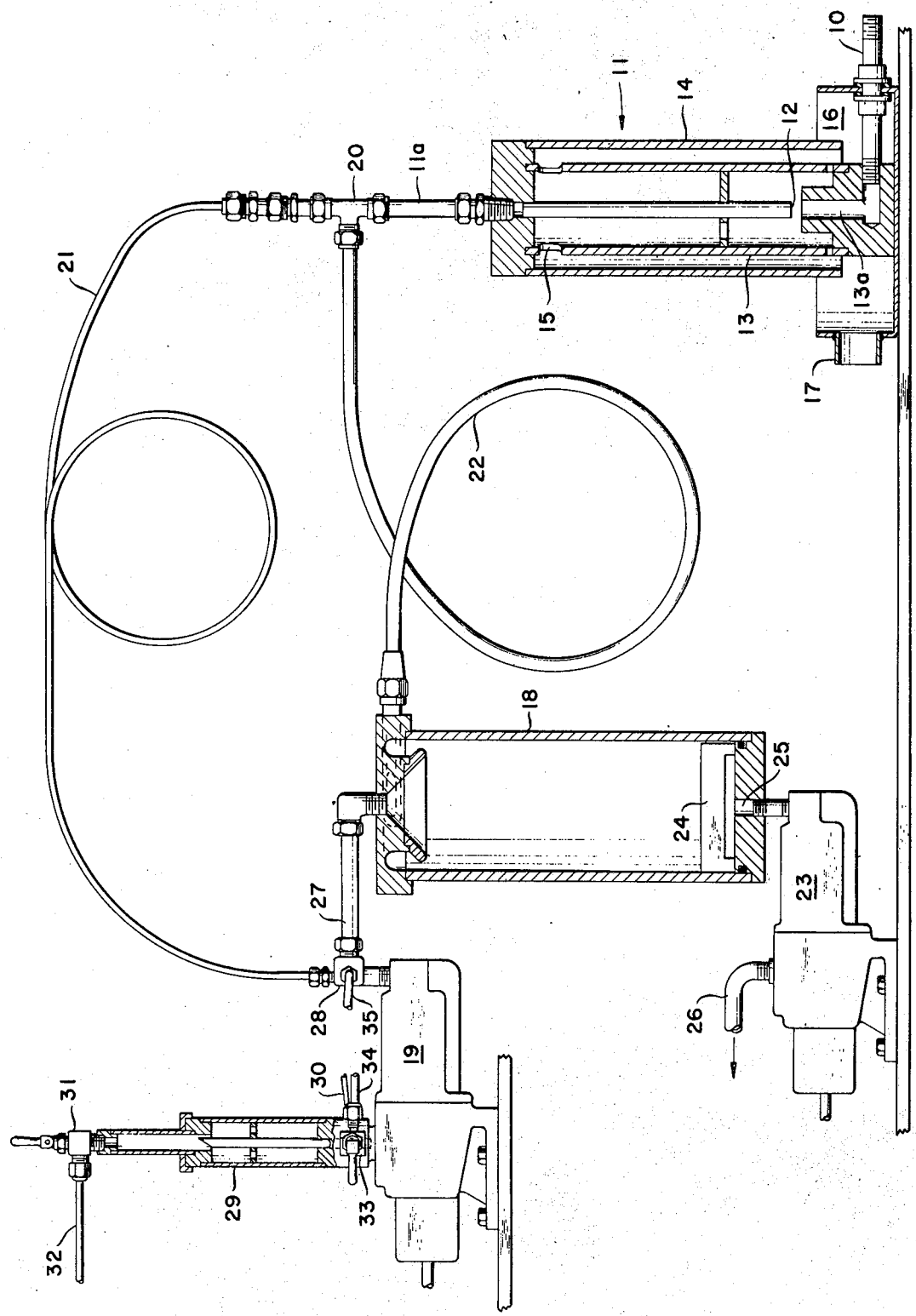
FIG. 2 is a diagrammatic view of a system for flash-distilling ground water samples in accordance with this invention.

FIG. 2 shows further details of a particularly suitable system for flash-distilling ground water in accordance with the present processs. The illustrated system contains a pressure equalization tank 11. The equalization tank can advantageously be used when the flow of ground water from a source, such as the water well 3 of FIG. 1, may undergo significant variations in rate or pressure. The incoming water is flowed into inlet 10.

The pressure equalization tank 11 ensures a constant inflow pressure by maintaining a constant height of water above the intake 12, from which the water flows to the gas extractor 18. The inflow pressure is kept constant by pumping more water than is needed into the concentric cylinders 13 and 14. Water enters the inside cylinder 13, through a large throat 13a at the bottom, and flows upward. The excess water overflows through slots 15 near the top. The overflow water passes between the inner and outer cylinders into a catchment basin 16 from which it is drained through outlet 17. As long as more water is supplied than is demanded by the extractor, the inner cylinder 13 is kept filled to the height of the slots. For example, where 6 gallons per minute are used, 10 gpm might be supplied. This creates the constant head. The water which is conveyed to the gas extractor 18 is caused to enter the intake 12 very close to the throat 13a of the inner cylinder. This reduces its mixing with water already in the equlization system.

Water is drawn from the pressure equlization tank 11 into the gas extraction cylinder 18 by the vacuum created by a gas pump 19. The water flows from intake 12, through a tube 11a, to a T 20. At the T the water is split into two streams: (1) lubrication water and (2) processed water.

The gas pump 19 is a positive displacement, noncontaminating pump, that is capable of functioning efficiently under cavitation. One suitable type of pump is a helical rotor, resilient stator, a high capacity pump, e.g., a type FS utility pump manufactured by Robbins and Myers, Inc., Mohno Pump Division, Springfield, Oh. Such pumps are capable of running many hours at a flow rate at which they cavitate. But, they can not be run dry, i.e., in the absence of lubricating liquid. In the present process, the pump lubrication is preferably supplied by the water that is being processed, in order to prevent contamination.

Pump 19 preferably creates a vacuum in the extraction chamber 18 that flash-boils the processed water. Such a vacuum equals the vapor pressure of the processed water at its ambient temperature, e.g., for water at 22°C the vapor pressure is 20 mm of mercury absolute. To achieve such a pressure, the gas pump must be "starved" (supplied only enough liquid to cool, seal, and lubricate the pump) and the extraction chamber must be partly, but incompletely, filled with liquid.

The pump-lubricating water is supplied to the pump through throttled conduit 21 while the processed water is supplied to the extraction chamber through throttled conduit 22. In a preferred embodiment the conduits 21 and 22 are relatively long slender flow beans. As used herein, the term "long slender flow bean" refers to a conduit through which the rate of flow of a given fluid (in response to a given pressure gradient) is determined primarily by the length and internal diameter of the conduit. The use of long slender flow beans as throttled conduits 21 and 22 is particularly advantageous since it causes the water to start losing gas as soon as it moves downstream from the main flow restriction within those conduits.

Where conduits such as conduits 21 and 22 have relatively large diameters and are provided with throttling valves, almost constant adjustment is required in order to maintain the proper rates of flow. On the other hand, where the conduits 21 and 22 are long slender flow beans having sizes and lengths adjusted for the pump capacity and liquid temperature the flow rates remain substantially constant (in respect to maintaining the required amounts of liquid within pump 19 and gas extraction chamber 18) without a need for adjusting throttling valves.

The processed water, carried through conduit 22, enters the extraction chamber 18 at the top, along a tangent to the cylindrical wall. This imparts a swirling motion to the water which causes it to flow down the inside of the wall as a sheet. Antiswirl fins 24 are mounted just above the exit 25 from the extraction chamber, in order to prevent the formation of a vortex at the intake of a scavenging pump 23. Such a vortex would not allow the scavenging pump to seal properly and thus the system could not maintain a good vacuum.

The scavenging pump 23 can comprise substantially any positive displacement pump having substantially the same characteristics as pump 19. It discards the degassed water through pump exhaust 26. The scavenging pump 23 is preferably run at a substantially constant rate, to remove fluid from chamber 18 at a substantially constant rate.

When liquid inflows through throttled conduit 22 at about the same rate at which liquid is removed by scavenging pump 23, the liquid level tends to remain constant within chamber 18. The vacuum in chamber 18 provides the force pulling liquid through conduit 22 and into the gas-filled upper chamber. The pump 23 and throttling action of conduit 22 keeps the liquid from filling the chamber.

In respect to gas pump 19 (where a similar low pressure is developed within the pump intake), the throttling action of conduit 21 keeps the pump from being filled by liquid. It keeps the lubrication water flow rate at less than the flow rate at which the pump is extracting gas.

From the gas extraction chamber 18, the separated gas outflows through conduit 27 and, via inlet cross 28, enters the gas pump 19. The gas output, together with the lubrication water from the gas pump, is discharged into a gas-liquid separating chamber 29. The separating chamber is mounted vertically above the gas pump exhaust. The entrained gas is gravity-separated from the lubrication water. The water is forced out through a throttled exhaust flow line 30 mounted in the base of the separator. Flow line 30 is preferably a long slender flow bean disposed to maintain a selected water level in separating chamber 29. The separated gas passes through a gas output toggle valve 31 and gas discharge line 32 into a sample back pressure control system (not shown).

Since the flow rate of lubrication water is preferably set to suit the requirements of gas pump 19, it is preferred that an exhaust flow bean serving as exhaust flow line 30 have a length and diameter chosen to discard this same amount of water when the pressure in the gas sample control system is at an optimum. A pressure too high will cause too much recombination of the sample gas with the lubrication water. A pressure too low will restrict the flow of the sample gas through the rest of the system and will thus increase the "lag time". Small variations in pressure ($\pm$ 0.1 psig) are automatically compensated for by corresponding changes in the water level in the separator, since, as the pressure is slightly below or above equilibrium, the water level rises or falls, respectively.

At the base of the separator 29, in addition to the exhaust flow line 30, there is a shutdown toggle valve 33. While the system is in operation, this valve is closed, but when it is desired to stop operations, the valve is opened to exhaust the separated lubrication water through line 34. Normally, the water level in the separator is held at ½ to ¾ full. A vacuum gage connection 35 is shown attached to inlet cross 28.

Preferred operating conditions and dimensions for the corresponding parts of the throttled gas extraction system for analyzing ground comprise the following. The back pressure in the gas sample control system can be about 11–13 psig. The vacuum in the extraction chamber 18 can be about 20 mm of mercury Abs. at 22°C. Experimental work showed that such a vacuum can be maintained if the gas pump 19 is lubricated with about 600–700 milliliters of water per minute. A flow of approximately 650 milliliters per minute can be obtained by using 11 feet of nylon tubing, 3/16-inch OD, 0.110-inch ID, for the lubrication flow bean 21. In supplying a gas analyzing system, a minimum of 125 milliliters of gas per minute is usually desirable. With the extractor arranged as indicated, ground water generally yields about 20–25 milliliters of extractable gas per gallon per minute. Thus, 6 gpm of processed water are sufficient. A processed water flow bean 22 made of 21 feet of ½-inch ID nylon tubing can carry a flow of about 6 gpm from the pressure equalization tank 11 into the extraction chamber 18. Where only a small volume is available, the volume can be reduced, e.g., to as little as about 2 gpm.

The gas analyzing system used in the present process can be substantially any that is capable of providing reproducible results and is arranged to provide a relatively rapid succession of measurements of hydrocarbon concentrations inclusive of the concentration of at least one hydrocarbon higher than methane. Suitable gas analyzing systems are known to those skilled in the art. Such systems are described in the J. B. Turner, H. L. Wise U.S. Pat. No. 3,645,131, for measuring hydrocarbon concentrations in a gas being circulated as a drilling fluid, and the H. L. Wise U.S. Pat. No. 3,685,345, for measuring the hydrocarbon concentration of a fluid being circulated within a borehole. A particularly suitable gas analyzing system, for using sample displacing and burning fluids free of heat-sensitive contaminates, is described in the H. L. Wise, A. Walters and R. G. Cook U.S. Pat. No. 3,695,844.

In the present process, the separated gas, i.e., that discharged through conduit 32 from separator 29, is preferably supplied through a means such as a multiple port valve which is arranged to switch a slug of gas, e.g., the gas that fills a trap-loop, into and out of a stream of a fluid being circulated through a chromatographic column to which a flame ionization detector is attached. As known to those skilled in the art, such a system can readily be arranged to periodically measure the concentrations of hydrocarbons in a succession of slugs of a gas such as that being accumulated by the flash-distillation of portions of ground water.

In the present process, such measurements are continued until the measured values become substantially constant. With an apparatus of the type described in the patents referred to above, and with a switch-valve arranged to initiate measurements of total hydrocarbon content at a rate of about 4 per minute, the attainment of such constant value results from the ground water in a particular location is usually accomplished within about 5 to 10 minutes. The hydrocarbon concentrations which are indicated as being representative of the ground water in that location, comprise such constant values.

In a particularly suitable procedure, measurements of total hydrocarbon are made on slugs of the extracted gas at a relatively rapid rate, e.g., about 4 per minute. Such measurements can be made by injecting slugs of about 2 cc in volume directly into the flame of a hydrogen flame chromatograph. Once a constant value has been obtained a somewhat larger slug, e.g., having a volume of about 8 cc, is injected into a chromatographic column that separately measures the concentrations of hydrocarbons having from 1–5 carbon atoms. A similar slug similarly analyzed in a column for separately measuring hydrocarbon containing from about 5–10 carbon atoms. Such chromatographic separations and concentration measurements usually require times in the order of about 5 minutes per sample.

In addition to the specified on-site hydrocarbon measurements, it is often desirable to measure the concentrations of other volatile constituents of the ground waters. Such additional measurements, i.e., concentrations of carbon dioxide, helium, etc., can be made on the site or can be made on collected samples of the gas released by the flash distillation. The gas samples for the additional measurements can be accumulated and stored and analyzed by conventional procedures. Such samples can advantageously be collected in glass containers suitable for direct attachment to mass spectrometer systems. Suitable additional measurements include C-13 isotope concentrations in $CO_2$, concentrations of helium, argon, hydrogen, etc. Such additional measurements are substantially unaffected by the storage of the samples.

What is claimed is:
1. A geochemical exploration process comprising:
   flowing successive portions of ground water from a selected subsurface location within the natural habitat of the ground water to a nearby surface location at rates sch that each portion arrives without significant chemical change;
   flash distilling gas inclusive of substantially all materials more volatile than water from successive arriving portions of the ground water substantially as soon as those portions reach the surface location;
   periodically measuring hydrocarbon concentrations inclusive of those of at least one hydrocarbon higher than methane in successively accumulated slugs of the gas substantially as soon as the slugs accumulate; and
   indicating as the hydrocarbon concentration of the ground water in the selected location a value that remains substantially constant throughout a plurality of the measurements.

2. The process of claim 1 in which each portion of a ground water is flowed from the subsurface location to the surface location within less than 1 hour.

3. The process of claim 1 in which pressures on successive portions of ground water are changed at substantially equal rates of change from substantially equal pressures greater than atmospheric to substantially equal pressures less than atmospheric that cause the water to boil at substantially the temperature of the subsurface location from which the water is flowed, so that substantially equal fractions of volatile components are flash-distilled from each so-treated portion of the ground water.

4. The process of claim 1 in which the gas is flash-distilled from the ground water by:
   pumping gas out of the upper portion of a chamber with a positive displacement pump that is capable of functioning under cavitation;
   flowing ground water into a lower portion of said chamber through a flow restricting conduit;
   pumping ground water out of the lower portion of said chamber with a positive displacement pump that is capable of functioning under cavitation;
   flowing ground water into said gas-pumping through a flow restricting conduit at a rate sufficient to lubricate the pump; and
   adjusting the flow rates through said flow restricting conduits so that said gas-pumping pump is lubricated while said chamber is evacuated to an extent sufficient to cause a significant amount of flash distillation in the ground water that enters it.

5. The process of claim 4 in which each of said flow restricting conduits is a relatively long slender conduit through which the rate of flow is determined primarily by the length and internal diameter of the conduit.

6. The process of claim 1 in which the slugs of the gas released from the ground water are accumulated and subjected to measurements of their total hydrocarbon content until the measured values become substantially constant.

7. The process of claim 6 in which measurements including measurements of the concentration of carbon dioxide are made on at least one slug of the so-extracted gas after a substantially constant measurement value has been obtained with respect to at least one hydrocarbon.

8. The process of claim 6 in which samples of the so-extracted gas are collected for subsequent analysis after said constant measurement value has been obtained.

9. The process of claim 6 in which measurements including measurements of the concentrations of hydrocarbons containing from about 1–5 carbon atoms are made after a substantially constant measurement value has been obtained with respect to at least one hydrocarbon.

10. The process of claim 9 in which measurements including measurements of the concentrations of hydrocarbons containing from about 5–10 carbon atoms are made after said constant measurement value has been obtained.

* * * * *